(12) United States Patent
O'Dell

(10) Patent No.: US 8,746,089 B2
(45) Date of Patent: Jun. 10, 2014

(54) APPARATUS FOR AUTOMATED POSITIONING OF EDDY CURRENT TEST PROBE

(75) Inventor: Thomas O'Dell, Issaquah, WA (US)

(73) Assignee: Babcock & Wilcox Nuclear Energy, Inc., Charlotte, NC (US)

( * ) Notice: Subject to any disclaimer, the term of this patent is extended or adjusted under 35 U.S.C. 154(b) by 729 days.

(21) Appl. No.: 12/687,261

(22) Filed: Jan. 14, 2010

(65) Prior Publication Data

US 2010/0181791 A1 Jul. 22, 2010

Related U.S. Application Data

(60) Provisional application No. 61/145,629, filed on Jan. 19, 2009.

(51) Int. Cl.
*F22B 37/10* (2006.01)
*B25J 11/00* (2006.01)
*B25J 15/00* (2006.01)
*G01M 99/00* (2011.01)

(52) U.S. Cl.
USPC ....... 73/865.9; 29/33 T; 73/113.01; 73/865.8; 414/745.3

(58) Field of Classification Search
USPC ....... 73/113.01, 865.8–865.9, 866.5; 29/33 T, 29/890.03; 137/315.01; 324/222; 348/84; 414/745.3, 814; 376/249; 901/41, 44, 901/46–47
See application file for complete search history.

(56) References Cited

U.S. PATENT DOCUMENTS

| 2,865,640 | A | * | 12/1958 | Watson et al. ............... 279/2.08 |
| 3,465,601 | A | * | 9/1969 | Schuhmann et al. ............. 74/45 |
| 3,495,546 | A | * | 2/1970 | Brown et al. ............ 73/866.5 X |
| 3,889,820 | A | * | 6/1975 | Ranger ........................ 414/676 |
| 3,913,752 | A |   | 10/1975 | Ward et al. |
| 4,004,698 | A |   | 1/1977 | Gebelin |
| 4,018,345 | A | * | 4/1977 | Formanek et al. .......... 165/11.2 |
| 4,018,346 | A | * | 4/1977 | Leshem et al. .............. 165/11.2 |
| 4,074,814 | A |   | 2/1978 | Cooper et al. |
| 4,193,735 | A |   | 3/1980 | Savor et al. |
| 4,298,054 | A |   | 11/1981 | Adamowski |
| 4,449,599 | A |   | 5/1984 | Creek |

(Continued)

FOREIGN PATENT DOCUMENTS

| CA | 1014724 A | 8/1977 |
| CN | 1045452 A | 9/1990 |

(Continued)

OTHER PUBLICATIONS

International Preliminary Report on Patentabilty for PCT/US2010/021407, report issued Aug. 2011.*

(Continued)

*Primary Examiner* — Thomas P Noland
(74) *Attorney, Agent, or Firm* — Goran P. Stojkovich

(57) ABSTRACT

An apparatus for automated inspection and repair of a tube sheet. The apparatus has a rotating gripper pod, comprising at least one tube gripper, a sliding body portion containing the gripper pod; a housing portion comprising at least one tube gripper and a tool head coupling. The tool head coupling swapably attaches to a eddy current test probe and at least one kind of tube repair tool. Novel, auto-locking tube grippers are also disclosed. A serial bus connects electronic modules within the apparatus and also connects the apparatus to an external controller.

8 Claims, 4 Drawing Sheets

(56) References Cited

U.S. PATENT DOCUMENTS

| | | | |
|---|---|---|---|
| 4,521,150 A * | 6/1985 | Pigeon et al. | 414/749.4 |
| 4,585,203 A | 4/1986 | Monne et al. | |
| 4,597,294 A | 7/1986 | Brill, III et al. | |
| 4,702,878 A * | 10/1987 | Klug et al. | 376/249 |
| 4,718,377 A * | 1/1988 | Haller | 414/745.3 X |
| 4,720,902 A * | 1/1988 | Gray | 29/890.047 |
| 4,829,648 A | 5/1989 | Arzenti et al. | |
| 4,895,029 A * | 1/1990 | Yamada et al. | 73/827 |
| 4,984,627 A * | 1/1991 | LeBourgeois | F22B 37/006 |
| 5,133,925 A | 7/1992 | Grypczynski et al. | |
| 6,450,104 B1 | 9/2002 | Grant et al. | |
| 6,820,575 B2 * | 11/2004 | Ashton et al. | 122/379 |
| 7,775,572 B2 | 8/2010 | Slack | |
| 7,909,120 B2 | 3/2011 | Slack | |
| 8,317,455 B2 * | 11/2012 | Mizelmoe | 414/814 |

FOREIGN PATENT DOCUMENTS

| | | |
|---|---|---|
| EP | 0063985 A1 | 11/1982 |
| EP | 0195454 B1 | 1/1991 |
| EP | 0852383 B1 | 11/2000 |
| FR | 2674938 | 10/1992 |
| JP | 59-97864 A | 6/1984 |
| WO | WO 9855730 A1 * | 12/1998 |
| WO | 2004009287 A1 | 1/2004 |

OTHER PUBLICATIONS

International Search Report for PCT/US2010/021407 mailed Aug. 8, 2011, 4 pages thereof.

* cited by examiner

APPARATUS FOR AUTOMATED POSITIONING OF EDDY CURRENT TEST PROBE

CROSS-REFERENCE TO RELATED APPLICATIONS

This application claims priority to, and the benefit of U.S. Provisional Application No. 61/145,629, filed Jan. 19, 2009 for all matter common to both applications. The disclosure of said provisional application is hereby incorporated by reference in its entirety.

BACKGROUND OF THE INVENTION

Regular inspection and testing of steam generator tube sheets is critical to the operation of a steam generator plant. Tube sheets are arrays of parallel tubes that can be accessed at least one end wherein the tube ends are arranged in an single plane. Testing of each tube is delicate and time consuming. In the past, this has been done by manually placing testing probes in the tubes. Described herein is an improved automated apparatus for positioning test and repair equipment in a tube sheet for steam generators.

Desirable attributes of such an automated apparatus include: single person fast installation; integrated grab features for handling; protection bumpers; independent of tube sheet and steam generator features; simplified cable systems and single point cable connection; simplified calibration; ease of decontamination; complete integration with data acquisition systems; fast, accurate performance; and support for repair tooling.

FIELD OF INVENTION

The present invention relates to automatic inspection and repair systems and more particularly to a robotic apparatus for positioning an eddy current test probe in an array of steam generator tubes.

BRIEF SUMMARY OF THE INVENTION

A robotic tool positioner especially adapted for positioning tooling and testing equipment in a tube array, such as in a steam generator. The tool positioner has several novel features, described herein.

In an embodiment, the tool positioner is adapted to move across the face of a tube sheet of open tubes. The positioner includes: a sliding body portion containing a rotating gripper pod with the rotating gripper pod having at least one tube gripper; left and right outer housing portions having at least one tube gripper each; and a tool head coupler to support various attachments, including an eddy current test probe, repair and maintenance tools. The sliding body portion moves laterally across the tube sheet with respect to the housing portion. The rotating gripper pod allows the positioner to rotate in an axis perpendicular to the plane of the tube sheet.

The tool head coupler provides for the attachment of test probes and repair and maintenance tools to the sliding body portion. The robot also includes machine vision and machine vision lighting.

In an embodiment, the tube grippers have a pneumatic actuator, at least one gripper shoes and integrated sensors adapted to detect deployment and retraction position. In an embodiment, the sensors are Hall effect sensors. The tube grippers are adapted so that the reactionary force of the tool positioner pulling away from the tube sheet forces the tube gripper shoes against the tube wall. To retract a tube gripper, the gripper head is pushed up into the tube slightly to release pressure on the gripper shoes, which are then retracted by spring-loaded retractors. In an embodiment, the robot electronics, including an on-board microprocessor, are interconnected by a simplified serial network that minimizes interconnection wires between electronic modules within the robot and allows for installation of new modules and interchangeability and updates to existing modules without costly wiring harness changes. The robot is controlled by an external controller that communicates with the robot over the simplified serial network. In an embodiment, the simplified serial network is the industry standard Controller Area Network or "CAN" bus.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF THE INVENTION

An inspection and repair robot is disclosed. The design provides a very efficient footprint for moving and repositioning eddy current test probes within a steam generator. The unique motion and small size provide high flexibility in reaching all tubes within the tube sheet without complex repositioning motions. This provides quick and efficient motion in positioning the robot to a target zone or specific tube. All of this is accomplished at state of the art speed. In an exemplary embodiment, the robot can transverse across the tube sheet at speeds of up to 5 feet per minute for large moves and can achieve tube-to-tube speeds during test or repair operations of up to 4 inches/second. The robot utilizes built-in machine vision for secondary tube verification for all attached tooling.

Robot Body

Figure 1:
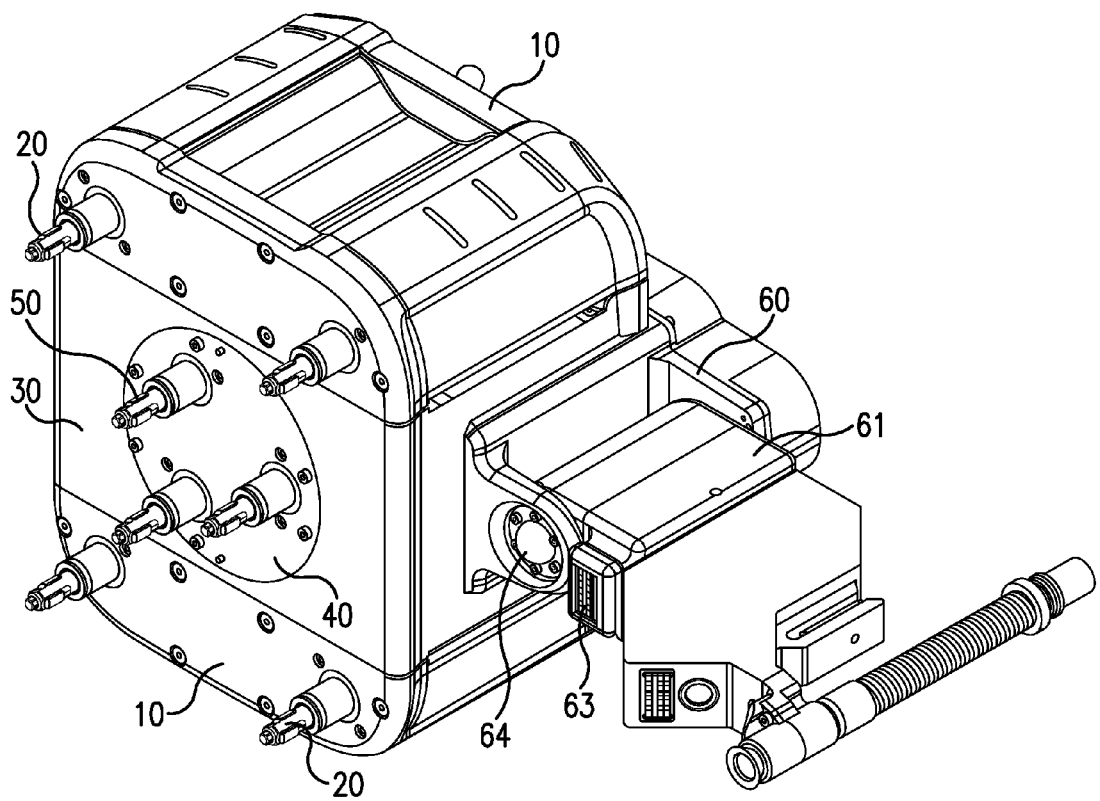
FIG. 1 is an isometric drawing of an exemplary design of an automated positioner.

With reference to FIG. 1, an exemplary repair and inspection robot has an outer housing 10 comprising four housing grippers 20; a sliding body center 30, comprising a rotating gripper pod 40, which has three grippers 50. The sliding body center 30 also has a tool head interface 60 comprising a tool head lock 61 with a hot shoe (not shown), machine vision lighting 63 and integrated machine vision camera 64. The tool head lock 61 is rotatably attached to the tool head bracket 60. The robot moves across a tube sheet (not shown) by alternately inserting and locking grippers 20, 50 into the tubes from either the outer housing 10 or the rotating gripper pod 40. It can be seen that when the three central grippers 50 are inserted into tubes, the outer housing 10 can rotate to any angle and translate a limited distance away from the rotating gripper pod 40 via the sliding relationship between the center body 30 and the outer housing 10. Once the outer housing 10 has repositioned itself with respect to the center body 30, the tube grippers 20 in the outer housing 10 are inserted into tubes and locked and the tube grippers 50 in the rotating pod 40 are released and withdrawn from the tube sheet. The sliding body 30 is then free to move with respect to the outer housing 10 to engage new tubes. This process is repeated until the housing 10 reaches the required location on the tube sheet.

The configuration of the four outer housing grippers 20 and three rotating pod grippers 50 is designed to support a broad range of square and tri-pitch tube sheet configuration, pitches and patterns. The body is designed to fit through the smallest man-way openings (not shown) in existing equipment. The controller for the robot is also as small as possible to maximize platform space. A small diameter control cable minimizes cable tangle.

Robot Positioning

In an exemplary embodiment, there is a host computer, which is outside the tube sheet environment. There is also an external controller in the tube sheet environment that communicates with the host computer and with the robot.

The host computer and software plans the robot movements and sends commands to the controller. It is typically remote to the radioactive environment where the robot and controller work. It sends commands through Ethernet to the controller which is external to the robot.

The controller communicates to the robot via a power/data cable that carries the CAN communication and power for the devices. The robot has multiple CAN devices for the specific functions. It receives and executes commands directly from the controller.

The controller has communication with both robot and host computer/software.

Sequences for robot moves from one position to another are determined by the host computer and transmitted to the robot external controller.

To make a move the external controller issues a command with arguments for the specific type of the device and an address for the device. For a motion axis, this may include commands for the motor on the axis in the form of rotation in degrees, rotation direction and rotation speed for an axis along with the address on the serial bus for the device.

The host computer software manages the logic of how to move and issues commands to the controller which in turns formats them in to the instructions for the devices described above.

Tube Inside Diameter Grippers

Figure 2:
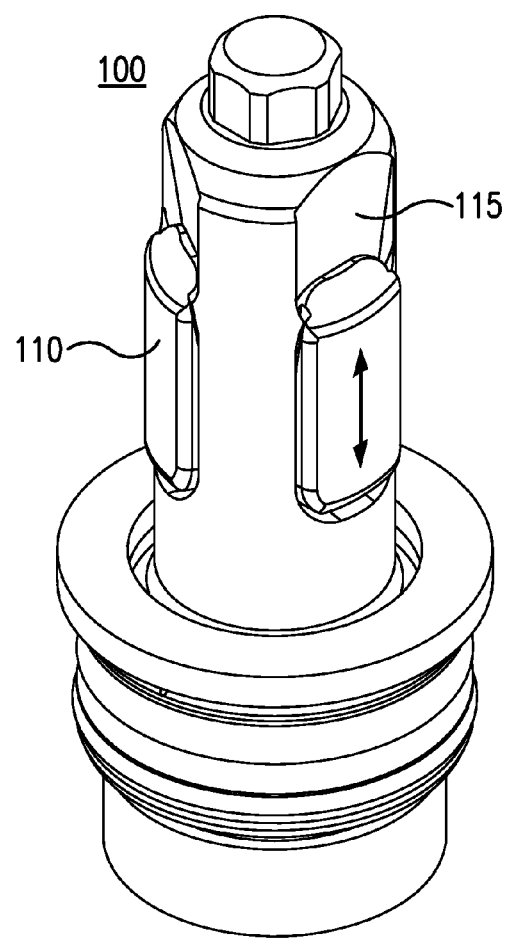
FIG. 2 is an isometric view of a tube gripper head.

FIG. 2 shows an exemplary tube gripper head 100. The gripper head 100 has three gripping shoes 110 that slide along three channels equally spaced around the outside wall of the gripper head 100. Each channel has an inclined surface 115 that is in contact with the gripper shoe 110. The inclined surface 115 forces the gripper shoe 110 away from the center of the gripper head 100 when the shoes 110 are pushed up into a tube (see FIG. 3), in a direction away from the robot body 10. As such, the grippers 20, 50 are self-locking. Once the shoes 110 are forced up into a tube, a force created by air pressure is exerted forcing the gripper bodies away from the tube sheet, thus forcing the shoes 110 against the tube wall 200. When the robot is below a tube sheet, the weight of the robot pulling down on the gripper head 100 keeps the shoes 110 locked against the tube wall 200, even if power is removed. When the tube sheet is not horizontal, reactionary force away from the tubes keeps the grippers 20, 50 locked. Any force tending to pull the robot away from the tubes will keep the grippers 20, 50 locked in place. The gripper shoes 110 are withdrawn only by forcibly retracting the shoes 110 while extending the gripper body slightly into the tube wall 200 to aid in pushing the shoes 110 back down the inclined surface 115 and away from the tube wall 200.

In an embodiment, the friction between the shoe 110 face and the inclined surface 115 is reduced by a friction reduction element (not shown). It is critical to the operation of the gripper shoes 110 that the friction between the shoe 110 and the inclined surface 115 be controlled so that less force is required to move the shoe 110 across the inclined plane than is required to move the shoe 110 across the tube wall 200. In an embodiment, a plastic insert 111 is inserted between the shoe 110 and the inclined surface 115.

Figure 3:
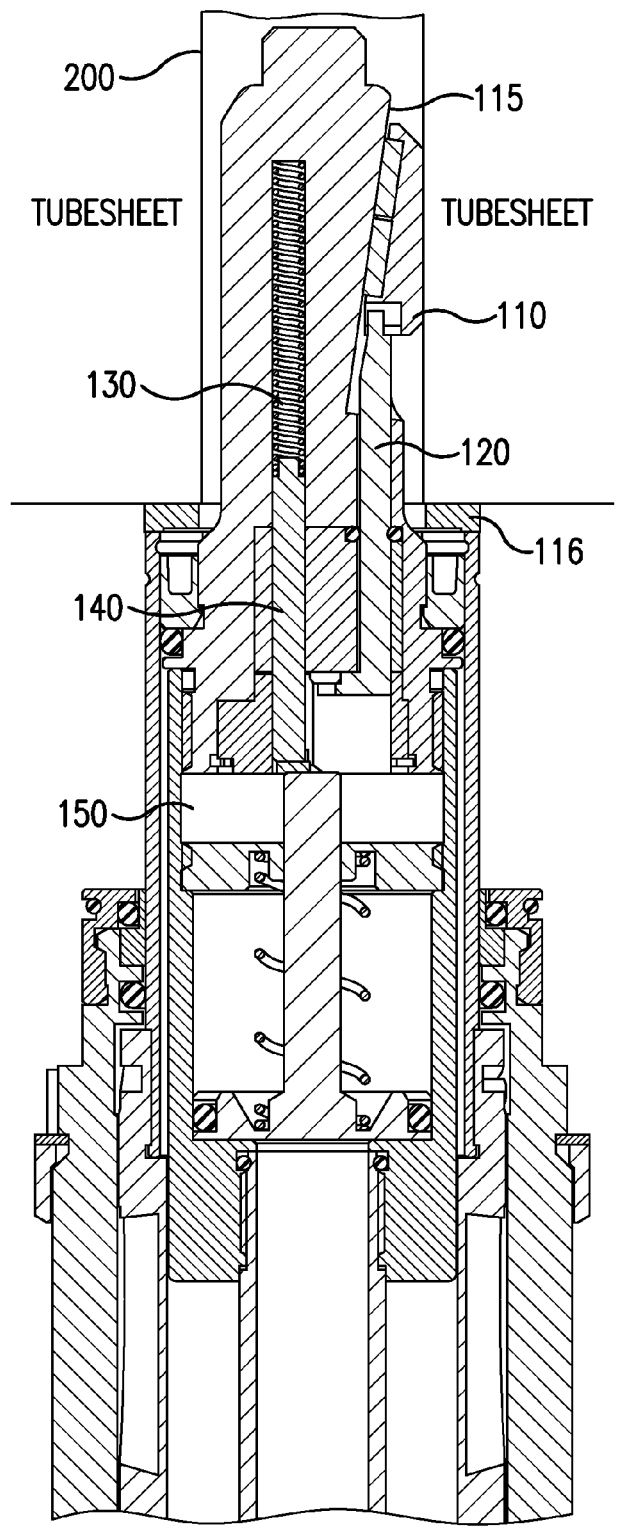
FIG. 3 is a cross-sectional drawing of an exemplary tube gripper inserted in a tube.

FIG. 3 is a cross section view showing a gripper head 100 inserted in a tube wall 200. A gripper shoe 110 is shown pressed against the wall 200, being forced into the wall 200 by the inclined surface 115 of the slot in the gripper head 100. In an exemplary design, each gripper shoe 110 is in contact with a pushrod 120. To lock the shoe 110 against the tube wall 200, the pushrod 120 is urged upward by a plate 150. When the plate 150 is retracted, spring 130 loaded return pins 140 urge the pushrods 120 back down, thus releasing outward pressure on the gripper shoes 110. As stated earlier, to aid in releasing the gripper shoes 110 from the tube wall 200, the entire gripper head assembly 100 is urged upward into the tube slightly, moving the inclined surface 115 up and releasing the outward pressure on the gripper shoes 110.

The embodiment shown is an advanced high performance gripper design that will not cause tube damage, yet provides high load capacity (of up to 300 lbs per gripper) and automatically provides grip force to match the load applied to the robot. All of this is accomplished while remaining fail-safe during power service interruptions.

Figure 4:
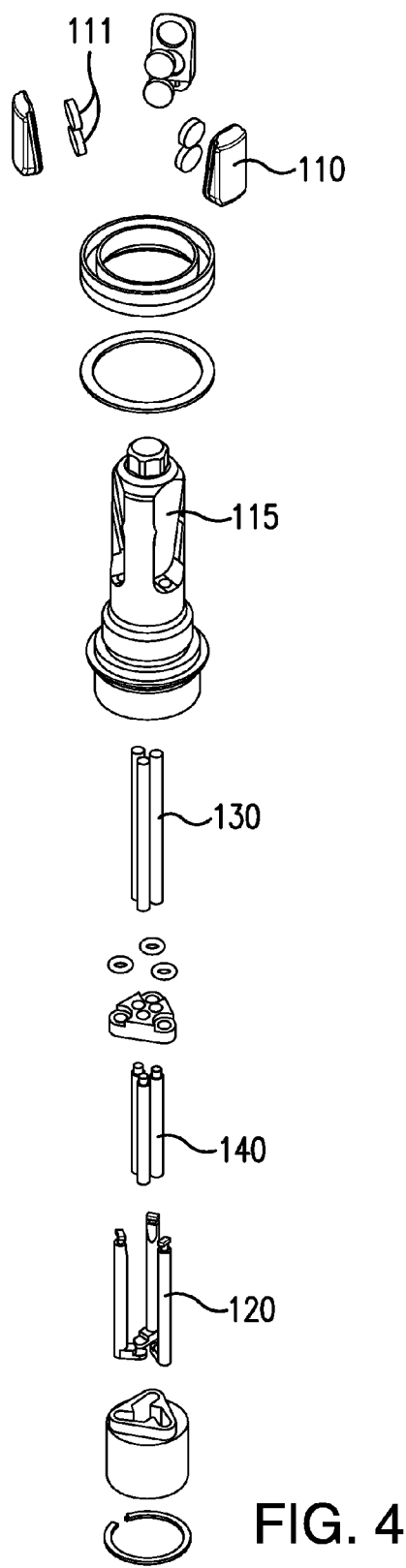
FIG. 4 is an exploded view of an exemplary tube gripper.

In an exemplary design, the robot tube grippers (FIGS. 2-4) have the following features: self locking tube ID gripper concept where the load of the robot helps lock and hold the lock; simultaneous deployment of gripper 110 and toe 116 along with the locking retract step; multi-stage custom air cylinder deployment/release mechanism, telescoping cylinders; simultaneously deploying, but individually retracting gripper shoes 110; individually replaceable gripper shoes; coatings or other friction reduction elements to provide slip plane surface between the gripper mandrel and shoe surface; hall effect, optical other type of sensor in the gripper head senses deployment status and senses plugs in the tube; multistage pneumatic locking gripper; robot load increases lock to tube surface; smooth gripper shoes do not impose stress points on tube wall, will not damage steam generator tubing; integrated hall sensors detect deployment and retraction position; failsafe grip during power interruptions; gripper heads are designed for quick change; and distributed I/O and onboard servo and control. Automatically and individually adjusting each gripper for optimum positioning of gripper within the tube inside diameter for accommodation of variances in tubing diameters for gripping and un-gripping operations.

In an embodiment, the position of the gripper within the tube is adaptively adjusted to account for variations in tube diameter and opening tolerances. There is an optimal depth range at which the gripper should be inserted into the tube. If the gripper is inserted too far into the tube, it is difficult to extract, since extraction requires extending the gripper slightly farther into the tube than the position where it is anchored. Anchoring the gripper to close to the open end of the tube can possibly damage the tube in some situations. Thus, it is useful to be able to locate the gripper in a limited insertion range in the tube. One way to do this is to include a position sensor on the gripper. The position sensor can be a Hall effect sensor or optical sensor. The gripper is inserted in the tube and locked and its position is determined. If the gripper is not in the desired area, the gripper is released and re-inserted. Positioning the gripper is a function of two timing parameters: there is a gripper insertion duration and a time at which the gripper shoes are forced outward to grip the tube wall. The combination of these two times is adjusted to place the gripper at differing depths within the tube. Because of variations in tube diameter and shape, the timing parameters are not universal. For this reason, an adaptive approach as described here is used to place the gripper in the desired location by adjusting the insertion time and shoe actuation time each time the gripper is repositioned until the gripper is anchored at the desired location in the tube.

Serial Network

In an exemplary embodiment, a serial network connects internal electronic modules of the robot. The serial network also connects any electronics attached to the tool head, the external controller and an installation robot. The serial network eliminates the need for custom wiring between these devices and reduces wire count, thus increasing reliability and reducing cost. The use of the serial network allows for expansion and improvements to existing hardware since additional modules can be added that communicate with the existing modules by simply tapping into the serial network. In an embodiment, the serial network is an electrical network and is implemented with the industry standard CAN bus. In an alternate embodiment, the serial network is a fiber optic network. The serial network also allows a single external controller to control multiple system elements within the robot system on the same bus. An additional serial network is provided in the form of a "1-Wire" memory chip to communicate and manage information stored in system components for use in controlling system level inventory, storing of data and configuration of software operations. The "1-Wire" network provides for insuring proper system operation parameters are respected to avoid undesirable operation.

Robot Tool Head

In an exemplary design, the robot tool head interface has the following features: quick make/break air coupling combined with electrical (power and signal) connection and proximity/Hall effect auto-lock feature.

Control Software

Software for an exemplary design includes: kinematics, multiple robot coordination, and collision detection/avoidance; software inspection planning & simulation; motion path planning algorithms to validate operation in bowl; trajectory planning algorithms to provide optimal path to target location; movement optimization algorithms to control movement around plugs and stays; and efficient inspection planning algorithms to optimize eddy current testing inspection and delivery of repair tooling.

Features and Benefits

Some features and benefits of the present invention include:

Small footprint of the robot provides ultimate maneuverability for efficient repositioning in all regions of the tube sheet while occupying less area thereby allowing the use of multiple robots per head.

Light Weight. At less than 40 lbs the robot is easily transportable and installable. In conjunction with the small footprint it requires less energy to grip into the tube sheet.

Fail-safe revolutionary gripper design ensures that the robot will remain attached to the tube sheet through loss of all power, yet remains easily removable during emergency situations.

Fast and strong with a tube-to-tube speed of up to 4 inches/sec and up to 300 lbs load capacity per gripper. The robot is capable of performing both high speed inspections and supporting the load demands of repair tooling.

A simplified system uses CAN-bus (Controller-area Network) control system architecture. The robot provides the smallest robot cable bundle in the industry with a diameter of less than 1 inch.

Intelligent software control manages the telemetry of all robots within a steam generator to avoid robot to robot collisions as well as probe collisions with robots operating in the opposite channel head.

Seamless Interface with Zetec's MIZ®-80iD intelligent system capabilities for exchange information between hardware components and tooling.

While the invention has been described in detail and with reference to specific examples thereof, it will be apparent to one skilled in the art that various changes and modifications can be made therein without departing from the spirit and scope thereof.

What is claimed is:

1. An apparatus for automated inspection and delivery of repair tooling to a tube sheet comprising open ended tubes having access to an inner tube diameter, said apparatus comprising:
   a sliding body portion containing a rotating gripper pod;
   said rotating gripper pod comprising three tube grippers,
   a housing portion comprising four tube grippers; and
   a tool head coupler, wherein said sliding body portion moves with respect to said housing portion.

2. The apparatus of claim 1, wherein each of said tube grippers comprises gripper shoes.

3. The apparatus of claim 2, wherein the tube gripper shoes are locked against the tube inner wall by reactionary force directed away from the tube.

4. An apparatus for automated inspection and delivery of repair tooling to a tube sheet comprising open ended tubes having access to an inner tube diameter, said apparatus comprising:
   a sliding body portion containing a rotating gripper pod;
   said rotating gripper pod comprising at least one tube gripper;
   a housing portion comprising at least one tube gripper; and
   a tool head coupler, wherein said sliding body portion moves with respect to said housing portion and wherein said tube gripper comprises:
   gripper shoes; and
   spring-loaded retractors in communication with said gripper shoes.

5. The apparatus of claim 4, wherein said gripper shoes have a tube contacting surface and an inner surface and said tube gripper further comprises a gripper shoe mating surface.

6. The apparatus of claim 2, further comprising spring-loaded retractors in communication with said gripper shoes.

7. The apparatus of claim 4, wherein said tool head coupler is part of one of said sliding body portion or said housing portion.

8. The apparatus of claim 4, wherein the tube gripper shoes are locked against the tube inner wall by reactionary force directed away from the tube.

* * * * *